(12) United States Patent
Gutmann

(10) Patent No.: US 6,784,176 B2
(45) Date of Patent: Aug. 31, 2004

(54) SOLVATES OF PYMETROZINE

(75) Inventor: Stephan Gutmann, Bad Säckingen (DE)

(73) Assignee: Syngenta Crop Protection, Inc., Greensboro, NC (US)

(*) Notice: Subject to any disclaimer, the term of this patent is extended or adjusted under 35 U.S.C. 154(b) by 0 days.

(21) Appl. No.: 10/039,706

(22) Filed: Nov. 9, 2001

(65) Prior Publication Data

US 2002/0099053 A1 Jul. 25, 2002

Related U.S. Application Data

(63) Continuation of application No. PCT/EP00/04251, filed on May 10, 2000.

(30) Foreign Application Priority Data

May 12, 1999 (CH) .............................. 0905/99
Sep. 3, 1999 (CH) .............................. 1606/99

(51) Int. Cl.⁷ ....................... C07D 253/06; A61K 31/53
(52) U.S. Cl. ..................... 514/242; 544/182
(58) Field of Search ............ 544/182; 514/242

(56) References Cited

U.S. PATENT DOCUMENTS 4,931,439 A    6/1990  Kristinsson ............ 548/132
5,384,403 A  * 1/1995  Rapold et al. ......... 544/182

OTHER PUBLICATIONS

Ali et al., Aust. J. Chem., 1996, vol. 49, pp. 927–930.
Leusen, Journal of Crystal Growth, 1966, vol. 166, pp. 900–903.

\* cited by examiner

Primary Examiner—Richard L. Raymond
Assistant Examiner—Venkataraman Balasubramanian
(74) Attorney, Agent, or Firm—Rose M. Allen

(57) ABSTRACT

Compounds of formula

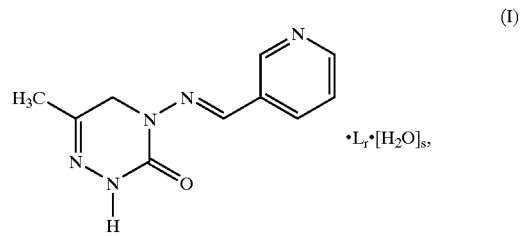

wherein
r and s, independently of each other, signify any value between 0.00 and 12.00; and
L is methanol, ethanol, propanol, isopropanol, butanol, isobutanol, t-butanol, cyclohexanol, tetrahydrofurfuryl alcohol, ethylene glycol, glycerol, methyl acetate, ethyl acetate, ethyl lactate, butyrolactone, ethylene carbonate, propylene carbonate, acetonitrile, dimethyl sulphoxide, dimethylformamide, dimethylacetamide, N-methyl-2-pyrrolidone, N-octyl-2-pyrrolidone, N-decyl-2-pyrrolidone, acetone, butanone, methyl isobutyl ketone, methylpropyl ketone, acetophenone, cyclohexanone, methylene chloride, trichloromethane, trichloroethane, tetrahydrofuran, diethylether, 1,2-dimethoxyethane, dioxane, methyl-tert.-butylether, ethanolamine, pyridine, chlorobenzene, toluene, xylene or tetramethylurea;
with the proviso that r and s are not simultaneously 0;
in each case in free form or in salt form, and their tautomers, in each case in free form or in salt form; a method for the preparation and usage of these compounds, their salts and their tautomers; pesticides whose active ingredient is selected from these compounds and their tautomers; and a method for the preparation of these solvates and where appropriate their salts, a method for the preparation of these compositions and their usage, are described.

8 Claims, No Drawings

SOLVATES OF PYMETROZINE

This application is a continuation of International Application No. PCT/EP00/04251, filed May 10, 2000, the contents of which are incorporated herein by reference.

The present invention relates to novel, insecticidally active solvates of pymetrozine, a method of producing them, compositions containing these compounds, a method of producing these compositions, a method of controlling pests with the said compositions, and their use in the control of animal pests, especially insects and members of the order Acarina, particularly in crops of cultivated plants.

Various solvates, for example hydrates, of a chemical compound can exhibit very different physical properties, which may lead to unforeseeable problems during technical preparation and processing of these compounds. The characteristics of such solvates frequently have a crucial influence on the separating ability (filtration), stirrability (crystal volume), surface activity (foaming), rate of drying, solubility, quality, formulating ability and storage stability (e.g. hygroscopy) of for example pesticidally active compounds. For example, the grinding and formulating properties, as well as the handling ability of such pesticidal mixtures, may be completely different depending on the respective solvatising. Since, in the various stages of synthesis of a preparation process, different physical properties of the respective synthesis products are of importance, it is especially advantageous to find the optimally suited solvation form for the respective stage of synthesis.

Pymetrozine is known for example from U.S. Pat. No. 4,931,439, in which the preparation is described in example P3. However, it cannot be assumed from this example that the product obtained had been solvated with ethanol, diethylether or water, even though the product had come into contact with ethanol, diethylether and water in the course of its preparation. At the end of the preparation process, the compound was dried, and it was used in the formulation examples as an essentially water-free and solvent-free product. Physical parameters such as temperature, humidity and pressure, which are crucial for the specific preparation of certain solvates, are not indicated anywhere in the said patent specification.

It is therefore the aim of the present invention to prepare solvates, in particular hydrates, and salts of such solvates of pymetrozine, the characteristics of which show the advantages mentioned initially, especially in the production and handling of pesticidal mixtures, particularly granulates.

Accordingly, the present invention relates to compounds of formula

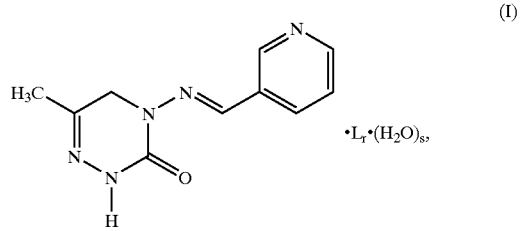

(I)

wherein
r and s, independently of each other, signify any value between 0.00 and 12.00; and
L is methanol, ethanol, propanol, isopropanol, butanol, isobutanol, t-butanol, cyclohexanol, atetrahydrofurfuryl alcohol, ethylene glycol, glycerol, methyl acetate, ethyl acetate, ethyl lactate, butyrolactone, ethylene carbonate, propylene carbonate, acetonitrile, dimethyl sulphoxide, dimethylformamide, dimethylacetamide, N-methyl-2-pyrrolidone, N-octyl-2-pyrrolidone, N-decyl-2-pyrrolidone, acetone, butanone, methyl isobutyl ketone, methylpropyl ketone, acetophenone, cyclohexanone, methylene chloride, trichloromethane, trichloroethane, tetrahydrofuran, diethylether, 1,2-dimethoxyethane, dioxane, methyl-tert.-butylether, ethanolamine, pyridine, chlorobenzene, toluene, xylene or tetramethylurea; with the proviso that r and s are not simultaneously 0;
in each case in free form or in salt form, and their tautomers, in each case in free form or in salt form, a method for the preparation and usage of these compounds, their salts and their tautomers; pesticides whose active ingredient is selected from these compounds and their tautomers; and a method for the preparation of these solvates and where appropriate their salts, a method for the preparation of these compositions and their usage.

In the following, a distinction will be made between the compound of formula (I) or the salts thereof, in which r and s are not simultaneously 0, and pymetrozine, which is the solvate-free compound (in which r and s are simultaneously 0).

Compounds of formula (I) have several basic centres. They may therefore form acid addition salts. These are formed for example with strong inorganic acids, such as mineral acids, e.g. perchloric acid, sulphuric acid, nitric acid, nitrous acid, a phosphoric acid or a hydrohalic acid, with strong organic carboxylic acids, such as $C_1$–$C_4$-alkanecarboxylic acids optionally substituted for example by halogen, e.g. acetic acid, such as optionally unsaturated dicarboxylic acids, e.g. oxalic, malonic, succinic, maleic, fumaric or phthalic acid, such as hydroxycarboxylic acids, e.g. ascorbic, lactic, malic, tartaric or citric acid, or benzoic acid, or with organic sulphonic acids, such as $C_1$–$C_4$alkanesulphonic or arylsulphonic acids optionally substituted for example by halogen, e.g. methanesulphonic or p-toluenesulphonic acid. In addition, compounds of formula (I) may form salts with bases. Suitable salts with bases are for example metal salts, such as alkali or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl, diethyl, triethyl or dimethylpropylamine, or a mono-, di- or trihydroxy-lower alkylamine, e.g. mono-, di- or triethanolamine.

In this case, on the one hand salts with formic acid, acetic acid and lactic acid are preferred, and on the other hand the sodium, potassium, magnesium and calcium salts are preferred, especially sodium salts. On the other hand, the compound of formula (I) in free form, i.e. in which r is 0, is also preferred.

Compounds (I) have also one acid group and can therefore form salts with bases. Suitable salts with bases are, for example, metal salts including metal complexes, such as alkali metal or alkaline earth metal salts, for example sodium, potassium or magnesium salts, but also comples salts with for instance copper, nickel of iron; or salts with ammonia or an organic amine, such as morpholine, piperidine, pyrrolidine, a mono-, di- or tri-lower alkylamine, for example ethyl-, diethyl-, triethyl- or dimethyl-propylamine, or a mono-, di- or trihydroxy-lower alkylamine, for example mono-, di- or triethanolamine. If appropriate, corresponding inner salts can furthermore be formed. Agrochemically advantageous salts are preferred in the context of the invention. Hereinabove and hereinbelow, the compounds (I) in free form are to be understood as including the corresponding salts, and the salts are to be understood as including the free compounds (I). In each case the free form is in general preferred.

Further preferred compounds of formula (I) are characterised in that L signifies methanol; especially wherein L is methanol and s is 0.

Additionally preferred compounds of formula (I) are characterised in that r signifies 0 and s is 0.5, 0.75, 1, 1.25, 1.5, 1.75, 2, 2.25, 2.5, 2.75, 3, 3.25, 3.5, 3.75, 4, 5, 6, 7, 8 or 12; especially 1, 1.25, 1.5, 1.75, 2, 2.25, 2.5, 2.75, 3, 3.25, 3.5, 3.75, 4, 5, 6, 7, 8 or 12; in particular 1.5, 1.75, 2, 2.25, 2.5, 2.75, 3, 3.25, 3.5, 3.75, 4, 5 or 6; most preferably 1.5, 2, 2.5, 3, 3.5 or 4; most particularly 2.

One especially preferred object of the invention is a compound of formula (I), in which r is 0 and s is 2 (pymetrozine dihydrate), and which shows the reflections listed in table 1 in the X-ray powder pattern.

TABLE 1

X-ray powder data of pymetrozine dihydrate

| d (Å) | Intensity |
|---|---|
| 12.4 | average |
| 7.1 | weak |
| 6.8 | very strong |
| 6.3 | weak |
| 6.2 | average |
| 5.82 | very weak |
| 5.40 | average |
| 5.14 | very weak |
| 4.85 | weak |
| 4.68 | very weak |
| 4.52 | very weak |
| 4.31 | very weak |
| 4.14 | weak |
| 4.08 | very weak |
| 3.96 | very weak |
| 3.83 | very weak |
| 3.71 | very weak |
| 3.58 | weak |
| 3.47 | very strong |
| 3.44 | very strong |
| 3.25 | strong |
| 3.21 | weak |
| 3.09 | average |
| 3.03 | weak |
| 2.99 | weak |
| 2.90 | weak |
| 2.82 | weak |
| 2.76 | weak |
| 2.57 | weak |

A further preferred object of the invention is a compound of formula (I) in which r is 1 and s is 0 and L is methanol (pymetrozine methanolate), and which shows the following reflections in the X-ray powder pattern:

TABLE 2

X-ray powder data of pymetrozine methanolate

| d (Å) | Intensity |
|---|---|
| 8.4 | strong |
| 6.3 | very weak |
| 5.96 | weak |
| 5.51 | very weak |
| 5.31 | very weak |
| 5.18 | very weak |
| 4.97 | very weak |
| 4.81 | very weak |
| 4.55 | average |
| 4.42 | weak |

TABLE 2-continued

X-ray powder data of pymetrozine methanolate

| d (Å) | Intensity |
|---|---|
| 4.22 | weak |
| 3.94 | very weak |
| 3.75 | very weak |
| 3.48 | strong |
| 3.38 | very strong |
| 3.25 | weak |
| 3.09 | weak |
| 3.04 | weak |
| 2.98 | very weak |
| 2.94 | very weak |
| 2.84 | very weak |
| 2.81 | very weak |
| 2.77 | very weak |
| 2.74 | very weak |
| 2.71 | very weak |
| 2.66 | weak |

A further object of the invention relates to a new modification of pymetrozine (hereinafter referred to as the pymetrozine β-modification), in which r and s are 0. This new modification is obtained whereby a sample of pymetrozine, which has been isolated during preparation from an aqueous-methanolic suspension, is dried at 120° C. to 150° C.

TABLE 3

X-ray powder data of pymetrozine β-modification

| d (Å) | Intensity |
|---|---|
| 9.7 | average |
| 8.4 | very weak |
| 5.87 | strong |
| 5.57 | average |
| 5.14 | very weak |
| 4.96 | weak |
| 4.86 | average |
| 4.69 | very weak |
| 4.40 | average |
| 4.29 | very weak |
| 4.23 | very weak |
| 3.83 | weak |
| 3.73 | weak |
| 3.66 | weak |
| 3.49 | strong |
| 3.34 | very strong |
| 3.28 | shoulder |
| 3.06 | weak |
| 2.95 | very weak |
| 2.82 | average |
| 2.65 | weak |
| 2.60 | very weak |
| 2.53 | very weak |
| 2.48 | very weak |
| 2.30 | weak |
| 2.25 | very weak |
| 2.20 | very weak |
| 2.11 | weak |
| 2.07 | weak |
| 2.00 | weak |

The X-ray powder data of the known α-modification of pymetrozine are also given below for comparison:

TABLE 4

X-ray powder data of pymetrozine α-modification

| d (Å) | Intensity |
|---|---|
| 11.9 | weak |
| 9.7 | average |
| 7.6 | average |
| 6.4 | very weak |
| 6.1 | average |
| 5.95 | average |
| 5.65 | average |
| 5.26 | average |
| 4.76 | weak |
| 4.49 | weak |
| 4.43 | very weak |
| 4.37 | weak |
| 4.11 | strong |
| 3.99 | very strong |
| 3.81 | weak |
| 3.57 | weak |
| 3.52 | weak |
| 3.48 | strong |
| 3.34 | very strong |
| 3.26 | very weak |
| 3.14 | strong |
| 3.07 | very weak |
| 2.99 | average |
| 2.90 | weak |
| 2.82 | average |
| 2.80 | weak |
| 2.75 | weak |
| 2.66 | very weak |
| 2.61 | weak |

Measurement of the X-ray powder patterns was made with an X'Pert powder diffractometer (Philips) with TTK camera (Anton Paar), using Cu radiation ($\lambda=1.54060$ Å). Measurements of the dihydrate of table 1 and of the anhydrates of tables 3 and 4 were made at room temperature. The measurement of the methanolate of table 2 was made whilst cooling (50°–8° C.) on a sample sealed with Kapton film.

It has now surprisingly been shown that dried, water-free and solvent-free pymetrozine is in a position to reversibly take up water or a solvent from the atmosphere or during mixing or grinding. It was found that, at room temperature and at a relative humidity of less than ca. 10%, water-containing pymetrozine gives up the water completely, and at a relative humidity of between 60% and 70%, takes up ca. 16 to 17% by weight of water again. The above-mentioned water content of 16 to 17% by weight corresponds very well to a dihydrate. Even pesticidal formulations that contain water-free and solvent-free pymetrozine take up usually water or the corresponding solvent from the atmosphere when left to stand under sufficiently high vapour pressure. This salvation, in particular water absorption, of formulations, in particular of water-dispersible powders and granulates, especially granulates, can lead to problems when handling and storing the pesticidal compositions, but these problems do not arise if pymetrozine in the form of a defined solvate or in the form of the above-mentioned β-modification is either introduced into the production process of the pesticidal composition, or is produced in an appropriate way during the afore-mentioned production process. For example, such formulations no longer have to be kept in airtight containers, and once containers have been opened, they do not have to be tightly sealed again in order to retain the quality of the goods.

In addition, the production of the formulations according to the invention with a relatively high water content or when using the β-modification of pymetrozine is simpler than the production of essentially water-free formulations or when using the α-modification, since production is generally effected in such a way that water is added in the formulation step and subsequently has to be removed again. To completely or almost completely remove the water involves considerable disadvantages, such as the high energy consumption, prolonged production times, greater use of equipment, etc.

A ready formulation of pymetrozine with a water content of ca. 10% by weight under normal conditions has only a very insignificant tendency to absorb moisture from the air, whereas a formulation whose water proportion has been reduced during production to less than 5% or which has been manufactured starting by using essentially waterfree ingredients is very hygroscopic. Long-term storage of formulations having a water content of less than ca. 5% by weight requires packaging that is completely sealed against water vapour and has to be produced using correspondingly greater effort. When it is disposed of, it presents greater problems than the conventional containers that are not absolutely watertight.

In addition, packages whose contents cannot be used up at once are generally not resealed in a sufficiently watertight manner. It is therefore unavoidable for water to be absorbed by the water-free formulation.

When a water-free formulation absorbs water, its quality is significantly reduced within a period of weeks to months. This means that the official figures relating to the proportion of active ingredient in the formulation can no longer be observed under some circumstances. Therefore, the absorption of water by the water-free formulation can lead to unsaleable goods when stored by the manufacturer or retailer, without the active ingredient actually decomposing.

Spontaneity: The quality of a water-dispersible granulate is determined to a substantial extent by its user friendliness. Accordingly, the user expects the granulate to completely break down into its primary particles within a few minutes of mixing up the spray liquor. When formulating pymetrozine, this characteristic known as spontaneity is not obtained if a formulation is used which is originally water-free or of low water content, but has absorbed water again during storage. In contrast to the essentially water-free formulations, after storing for a period of 7 days in the appropriate test apparatus, the formulations according to the invention show a complete breakdown of the granulates into the primary particles within a few minutes.

TABLE 5

Comparison of spontaneity after various periods (test carried out analogously to CIPAC MT 174); pymetrozine granulates with a content of active ingredient of 50% by weight

| | | spontaneity without storage in % | | spontaneity after open storage for 7 days at room temperature in % | | |
|---|---|---|---|---|---|---|
| time | water % by weight | 0.5 min | 1 min | water % by weight | 0.5 min | 1 min |
| granulate I | 5.1 | 95 | 98 | 13.2 | 25 | 31 |
| granulate II | 10.3 | 96 | 98 | 13.7 | 93 | 98 |

When measuring the spontaneity, first the spray liquor is produced by shaking the composition in a cylinder in the presence of a specified amount of water. After 0.5 or 1 minutes, 90% of the liquor is suctioned off and the remainder concentrated by evaporation. The residue obtained is assessed after drying and the amount of the originally used material which is suspended in the liquor is calculated in %.

Without taking into account the water content, the granulates have the composition as indicated in the following example F10 and are produced as indicated therein.

Further advantages of the formulations being claimed according to the invention are improved suspension ability in the spray liquor and improved dispersibility.

A desired solvate may be produced before the active substance is combined with the formulation excipients, or alternatively during the formulation procedure by suitably bringing it into contact with the desired amount of a certain solvent or with water. It is therefore possible to use various processes for the specific production of such solvates and of pesticidal compositions containing such solvates. Water-free and solvent-free pymetrozine can for example be agitated or ground in a mixer in an atmosphere having a defined content of water or solvent until the desired form is obtained. Or, pymetrozine with a high content of water or solvent, which results from a production process, or which has been produced by mixing essentially solvent-free and water-free pymetrozine specifically with a larger amount of solvent or water, is dried in a drier to the desired content of solvation agent. These methods of producing solvates, especially hydrates, or pymetrozine, therefore form a further object of the present invention.

Suitable formulations for the compounds of formula (I) are described for example in U.S. Pat. No. 4,931,439. They are all characterised in that they do not contain any pymetrozine in solvated form.

The formulations, i.e. agents, preparations or compositions which contain an active ingredient of formula (I) and one or more solid and/or liquid formulation excipients, likewise form an object of the invention. They are produced for example in a manner known per se, by intimately mixing and/or grinding the active ingredient of formula (I) with the formulation excipients, such as solvents or solid carriers. An alternative, new preparation method, which similarly forms an object of the invention, consists in adding the solvation agent during the formulation procedure, thus forming the solvate during the formulation process. In an important variant of this method, the solvation agent can be added in excess, and removed again at the end for example by evaporation, to give the desired value. In the case of certain mixtures, this procedure can significantly simplify the production process. Corresponding compositions produced by this method similarly form an object of the invention.

Surface-active compounds (surfactants) may additionally be used for preparing the formulations. Examples of solvents and solid carriers are given e.g. in U.S. Pat. No. 4,931,439. Depending on the type of active ingredient of formula (I) to be formulated, suitable surface-active compound are non-ionic, cationic and/or anionic surfactants and surfactant mixtures having good dispersing and wetting properties. Examples of suitable anionic, non-ionic and cationic surfactants are listed for example in U.S. Pat. No. 4,931,439.

The insecticidal and acaricidal formulations according to the invention will as a rule contain from 0.1 to 99% by weight, especially from 1 to 95% by weight, of compound of formula (I), from 1 to 99.9% by weight, especially from 5 to 99.8% by weight, of a solid or liquid formulation excipient, and from 0 to 25% by weight, especially from 0.1 to 25% by weight, of a surfactant. Equally preferred are the insecticidal and acaricidal formulations which contain from 0.1 to 94% by weight, especially from 0.1 to 90% by weight, of pymetrozine, from 5 to 30% by weight of solvation agent, from 1 to 94.9% by weight, especially from 5 to 90% by weight, of a solid or liquid formulation excipient, and from 0 to 30% by weight, especially from 0.1 to 25% by weight, of a surfactant.

The pesticidal formulations, especially granulates, that are preferred in particular, are those which contain from 3 to 5% by weight, or those which contain from 30 to 50% by weight of pymetrozine. Equally preferred are water-dispersible powders, which contain from 25 to 50% by weight of pymetrozine.

Also preferred are pesticidal formulations, in particular granulates, which contain from 8 to 40% by weight, preferably from 8 to 20% by weight, especially from 8 to 14% by weight, of water. Equally preferred are pesticidal formulations, in particular granulates, which contain from 40 to 60% by weight of pymetrozine, especially 50% by weight of pymetrozine.

Also preferred are wettable powders which contain from 6 to 20% by weight, especially from 8 to 12% by weight, of water, and from 20 to 30% by weight of pymetrozine, especially 25% by weight of pymetrozine.

When specifying the amount of water content, the fact that the formulation excipients themselves often have a certain residual content of water must be taken into consideration. For this reason, the water content of the formulations actually ascertained is generally a little higher than that calculated from the composition of the hydrates. In general the measured contents are 1 to 5% by weight higher than those calculated. Hereinbefore and hereinafter, a formulation of pymetrozine that is essentially free of water or of low water content is understood to be a pesticidal mixture containing at most 6% by weight of water, based on the total mixture.

Whereas it is preferred to formulate commercial products as concentrates, the end user will normally use dilute formulations. The compositions may also contain further ingredients, such as stabilisers, e.g. where appropriate epoxidised vegetable oils (epoxidised coconut oil, rapeseed oil, or soybean oil), activators, antifoams, typically silicone oil, preservatives, viscosity regulators, binders, tackifiers, as well as fertilisers or other active ingredients.

The compounds of formula (I) are usually applied to the plants or the locus thereof in concentrations of 0.001 to 1.0 kg/ha, preferably 0.1 to 0.6 kg/ha. The concentration required to achieve the desired action can be determined by experimentation. It will depend on the type of action, the development stage of the cultivated plant and of the pest, as well as on the application (locus, time, method), and as a result of these variables can vary over a wide range. As with the type of compositions, the methods of application such as spraying, atomising, dusting, wetting, scattering or pouring, are selected in accordance with the intended objectives and the prevailing circumstances.

The compositions which contain the compounds of formula (I) have excellent insecticidal properties, making them suitable for application in crops of cultivated plants, especially in cereals, cotton, soybeans, sugar beet, sugar cane, plantations, rape, maize and rice. Crops will also be understood to mean those crops that have been made tolerant to pesticides by conventional breeding or genetic engineering methods. Pests, especially insects and members of the order Acarina, that may be controlled with the formulations according to the invention, are described for example in U.S. Pat. No. 931,439 and in U.S. Pat. No. 46,145.

The invention is illustrated by the following non-limitative Examples.

FORMULATION EXAMPLES

% refer to percentages by weight

| Example F1: Emulsion concentrates | a) | b) | c) |
|---|---|---|---|
| pymetrozine methanolate | 2.5% | 4.0% | 0.5% |
| calcium dodecylbenzene sulphonate | 5% | 8% | 6% |
| castor oil polyethylene glycol ether (36 mol EO) | 5% | — | — |
| tributyl phenol polyethylene glycol ether (30 mol EO) | — | 4% | 4% |
| lactic acid | 80% | 71% | — |
| formic acid | — | — | 64.5% |
| N-octylpyrrolidone | 7.5% | 5% | 20% |

Emulsions of any desired concentration can be prepared from such concentrates by dilution with water.

|  | a) | b) | c) |
|---|---|---|---|
| Example F2: Solutions |  |  |  |
| pymetrozine trihydrate | 30% | 20% | 10% |
| formic acid | 70% | — | — |
| acetic acid | — | 80% | — |
| lactic acid | — | — | 90% |
| Example F3: Solutions |  |  |  |
| pymetrozine methanolate | 30% | 20% | 10% |
| formic acid | 70% | — | — |
| acetic acid | — | 80% | — |
| lactic acid | — | — | 90% |

The solutions are suitable for use in the form of microdrops.

| Example F4: Coated granulates | a) | b) | c) |
|---|---|---|---|
| pymetrozine * CH₃OH | 5% | 3% | 2.5% |
| highly dispersed silicic acid | 6% | 5% | 4% |
| polyethylene glycol 300 | 5% | 4% | 3% |
| calcium carbonate | 84% | 88% | 90.5% |

The active ingredient is suspended in polyethylene glycol 300, sprayed onto the carrier and the granulates subsequently powdered off with the silica.

| Example F5: Dusts | a) | b) |
|---|---|---|
| pymetrozine dihydrate | 2% | 5% |
| highly dispersed silicic acid | 1% | 5% |
| talc | 97% | — |
| kaolin | — | 90% |

Ready-to-use dusts are obtained by intimately mixing the carriers with the active ingredient and subsequently grinding.

| Example F6: Wettable powders | a) | b) | c) |
|---|---|---|---|
| pymetrozine dihydrate | 25% | 50% | 75% |
| sodium lignin sulphonate | 5% | — | 8% |
| sodium lauryl sulphate | 3% | — | — |
| sodium diisobutylnaphthalene sulphonate | — | 6% | 8% |
| octylphenol polyethylene glycol ether (7–8 mol EO) | — | 2% | — |
| highly dispersed silicic acid | 5% | 10% | 9% |
| kaolin | 62% | 27% | — |

The compounds are mixed with the adjuvants and this mixture is ground in a suitable mill to give wettable powders which can be diluted with water to give suspensions of any desired concentration.

| Example F7: Wettable granulate | a) | b) | c) |
|---|---|---|---|
| pymetrozine dihydrate | 30% | 40% | 85% |
| sodium lignin sulphonate | 30% | 30% | 12.8% |
| sodium dibutylnaphthalene sulphonate | 5% | — | 2.0% |
| block polyoxyalkylate | 5% | 7.5% | — |
| polymeric organic carrier | 5% | — | — |
| antifoam | 0.1% | 0.2% | 0.2% |
| kaolin | 24.9% | — | — |
| talc | — | 22.3% | — |

The active ingredient is mixed and ground with the adjuvants, and the mixture is moistened with water. This mixture is extruded, granulated and then dried in a stream of air.

| Example F8: Suspension concentrate | |
|---|---|
| pymetrozine dihydrate | 40% |
| propylene glycol | 5% |
| nonylphenol polyethylene glycol ether (15 mol EO) | 6% |
| tristyrylphenol polyglycol ether phosphate triethanolamine | 7% |
| heteropolysaccharide | 1% |
| 1,2-benzisothiazol-3-one | 0.2% |
| silicone oil in the form of a 75% aqueous emulsion | 0.8% |
| water | 40% |

The finely ground active ingredient is intimately mixed with the adjuvants. In this way, a suspension concentrate is obtained from which suspensions of any desired concentration can be prepared by dilution with water.

Example F9

Preparation of a Water-Dispersible Granulate of the Compound of Formula (I)

The following substances are admixed and subsequently ground using a conventional mill:

| | |
|---|---|
| 60% | anhydrous pymetrozine |
| 5% | sodium dibutylnaphthalene sulphonate |
| 10% | sodium lignin sulphonate |
| 5% | sodium sulphate |
| 15% | polymeric organic carrier |
| 0.1% | perfluoroalkyl phosphoric acid |
| 4.9% | silicon dioxide |

The mixture is subsequently mixed with 35–45% by weight water and granulated. After drying to residual moisture of 8–12% on a commercial continuous drier, the granulate obtained is sieved to a defined grain size. Granulates are obtained, which contain the compound of formula (I) in hydrated form.

Example F10

Preparation of a Water-Dispersible Granulate of the Compound of Formula (I)

The following substances are admixed.

| | |
|---|---|
| 50% | anhydrous pymetrozine |
| 5% | sodium dibutylnaphthalene sulphonate |
| 10% | sodium lignin sulphonate |
| 5% | sodium sulphate |
| 15% | polymeric organic carrier |
| 0,1% | perfluoroalkyl phosphoric acid |
| remaining % | silicon dioxide |

The mixture is subsequently mixed with 50 to 70% by weight water and granulated. After drying to residual moisture of 8–12% on a commercial continuous drier, the granulate obtained is sieved to a defined grain size. Granulates are obtained, which contain the compound of formula (I) in hydrated form.

Preparation Examples of Solvates of Formula (I) and of Formulations Containing such Solvates Example P1

Preparation of the Compound of Formula (I), in which r is 0 and s is 2 (dihydrate of pymetrozine)

Pymetrozine is stored in a closed container having controlled atmosphere of 89% relative humidity for a period of 10 days. The product is then removed from the container and equilibrated in a laboratory atmosphere. On a thermo-scale, the product obtained shows a weight loss of 13.9% between room temperature and 125° C., which corresponds to two water molecules (theoretical loss 14.2%).

In the X-ray diffractometer using Cu radiation ($\lambda$1.54060 Å) at room temperature, the pattern reproduced in Table 1 is found.

Example P2

Preparation of the Compound of Formula (I), in which r is 0 and s is 2 (dihydrate of pymetrozine)

In a mixer, a defined amount of water (16% based on water-free pymetrozine) is sprayed evenly onto the active ingredient whilst cooling, and the powder is subsequently slowly stirred until cooled to room temperature.

Example P3

Preparation of the Compound of Formula (I), in which r is 0 and s is 2 (dihydrate of pymetrozine)

In a rapid-action mixer, a defined amount of water is sprayed evenly onto a mixture of active ingredient and formulation excipients, and after interim storing, the powder is further processed to the final formulation.

Example P4

Preparation of the Compound of Formula (I), in which r is 0 and s is 2 (dihydrate of pymetrozine)

In a vessel with stirrer, pymetrozine is suspended in water in the presence of the remaining formulation components, and the mixture is subsequently finely sprayed in a stream of air and dried to residual moisture of 6–15%.

Example P5

0.5 g of Pymetrozine are stirred for 9 days at 25° C. in 2.5 g of water; then the suspension is filtered. The dihydrate, which in thermogravimetry shows a weight loss of 12% by weight, is obtained.

Example P6

Preparation of the Compound of Formula (I), in which r is 1, s is 0 and L is methanol (methanolate of pymetrozine)

0.488 g of water-free pymetrozine are added at 0° C. to 1.909 g of water-free methanol and stirred for 7 days at 0° C. The suspension is filtered through a frit without applying a vacuum. A sample of the filter cake is immediately measured in the X-ray diffractometer. The pattern given in Table 2 is obtained. A thermogravimetric examination between 0° C. and 100° C. shows a weight loss of 12.4%, which corresponds to one molecule of methanol (theory: 12.8% by weight).

What is claimed is:
1. A compound of formula

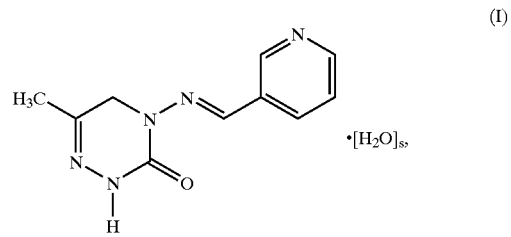

(I)

in essentially pure form, wherein s is 2.

2. A method for the preparation of a compound of formula (I) as described in claim 1, in which a non-solvated, pesticidally active compound of the formula:

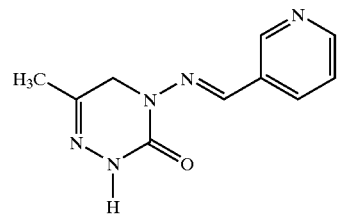

is brought into contact with water.

3. A method for the preparation of a pesticidal composition which contains a compound according to claim 1 of formula (I) and one or more adjuvants, which comprises intimately mixing or grinding an essentially solvate-free compound of formula

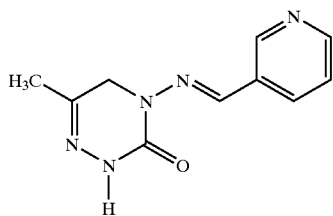

together with the formulation excipients and with water.

4. A method for the preparation of a pesticidal composition which contains a compound according to claim 1 of formula (I) and one or more adjuvants, which comprises intimately mixing or grinding the active ingredient of formula (I) with the formula excipients.

5. A method for the preparation of a pesticidal composition which contains a compound according to claim 1 of formula (I) and one or more adjuvants, which comprises bringing a pesticidal mixture containing an essentially solvate-free compound of formula

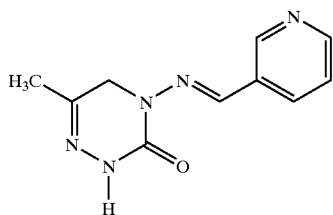

in contact with in excess of water, and the water removed again at the end for example by evaporation.

6. A pesticidal composition which contains a compound of formula (I)

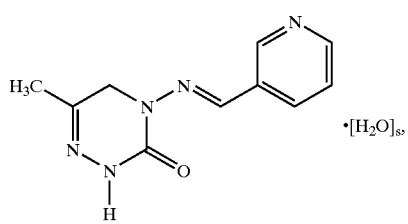

(I)

in essentially pure form, wherein s is 2; and one or more adjuvants, prepared according to the method as described in claim 3.

7. A pesticidal composition which contains a compound of formula (I)

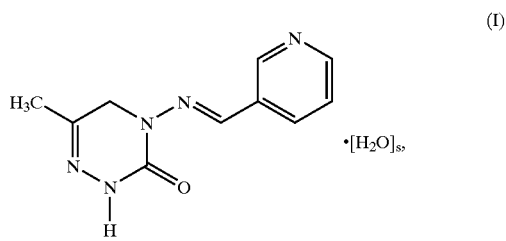

(I)

in essentially pure form, wherein s is 2; and one or more adjuvants, prepared according to the method as described in claim 4.

8. A pesticidal composition which contains a compound of formula (I)

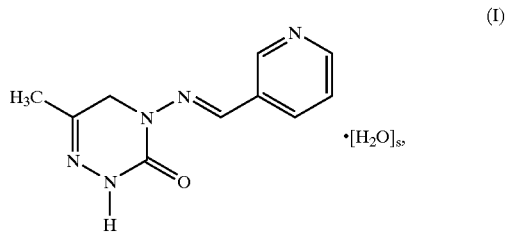

(I)

in essentially pure form, wherein s is 2; and one or more adjuvants, prepared according to the method as described in claim 5.

* * * * *